United States Patent [19]
Kocache

[11] Patent Number: 5,369,980
[45] Date of Patent: Dec. 6, 1994

[54] METHOD AND APPARATUS FOR THE DETERMINATION OF THE PROPORTION OF A PARAMAGNETIC GAS IN A GAS MIXTURE

[75] Inventor: Riad M. A. Kocache, Crowborough, England

[73] Assignee: Servomex (UK) Ltd., Sussex, England

[21] Appl. No.: 30,199

[22] PCT Filed: Sep. 23, 1991

[86] PCT No.: PCT/GB91/01631
§ 371 Date: Mar. 24, 1993
§ 102(e) Date: Mar. 24, 1993

[87] PCT Pub. No.: WO92/05436
PCT Pub. Date: Apr. 2, 1992

[30] Foreign Application Priority Data
Sep. 25, 1990 [GB] United Kingdom ............... 9020853.9

[51] Int. Cl.⁵ .......................................... G01N 27/74
[52] U.S. Cl. ..................................... 73/25.02; 324/204
[58] Field of Search ............... 73/25.02, 24.01; 324/204, 201

[56] References Cited

U.S. PATENT DOCUMENTS

| | | | |
|---|---|---|---|
| 3,672,388 | 6/1972 | Ringwoll | 73/24.01 |
| 3,742,344 | 6/1973 | Hummel | 73/24.01 |
| 4,563,894 | 1/1986 | Karrer | 73/24.01 |

Primary Examiner—Hezron E. Williams
Assistant Examiner—Michael J. Brock
Attorney, Agent, or Firm—Cumpston & Shaw

[57] ABSTRACT

A method and apparatus for determining the proportion of a paramagnetic gas in a mixture of gases is disclosed. There is provided an element which is able to oscillate in a magnetic field. A force acting on the element due to the presence of paramagnetic gas in the magnetic field changes according to the concentration of paramagnetic gas present. This change in force affects parameters of the oscillation such as damping and frequency, which may be monitored thereby to determine the concentration of paramagnetic gas present.

29 Claims, 2 Drawing Sheets

METHOD AND APPARATUS FOR THE DETERMINATION OF THE PROPORTION OF A PARAMAGNETIC GAS IN A GAS MIXTURE

FIELD OF THE INVENTION

The present invention relates to a method and apparatus for the determination of the proportion of a paramagnetic gas such as oxygen in a mixture of gases which are not all paramagnetic.

BACKGROUND OF THE INVENTION

Various methods have been proposed in the past for detecting gases in gaseous mixtures. Faraday showed in the last century that all matter is magnetic. Matter strongly attracted to a magnetic field was termed paramagnetic and matter repulsed by a magnetic field was termed diamagnetic. Few gases have strong paramagnetic properties, amongst those with the strongest are oxygen $O_2$, nitrogen dioxide $NO_2$ and nitrous oxide $NO$.

This property exhibited by only a few gases has been used in the past for the determination of the proportion of a paramagnetic gas, usually oxygen, in a gas mixture using generally four methods:

1. Magnetic Wind. This method suffers from effects such as thermal conductivity of background gases, low sensitivity, long response time and is not used much nowadays.
2. Differential Pressure. This method requires a reference gas and in some forms requires an alternating magnetic field. It can be made to have a somewhat fast response, but the smallness of the differential pressure created requires very sensitive flow sensors.
3. Magnetic Auto-balance. A torsion balance with automatic feed back control via an optical system. The most popular method, but suffers mainly from slow response time, and gas flow errors.
4. Relative Change in Permeability. Many different approaches to this method have been attempted without a great deal of success due to the extreme smallness of the resulting change in permeability.

Thus there remains a need for a method and apparatus for the determination of a proportion of paramagnetic gas in a mixture of gases which is relatively simple to use and has a quick response to changes in the gas mixture being measured.

SUMMARY OF THE INVENTION

The present invention provides a method of determining the proportion of a paramagnetic gas in a mixture of gases comprising:
  providing a magnetic field and a resiliently mounted member in said magnetic field;
  causing said resiliently mounted member to oscillate;
  determining the value of at least one specified parameter of the oscillation whereby to determine the proportion of a paramagnetic gas in the mixture of gases surrounding said resiliently mounted member.

It is well established that the magnetic force F acting on an element, a sphere for example but not necessarily, of a volume magnetic susceptibility $K_o$, a volume V and a mass M placed in a magnetic field of strength H and a gradient $dH/dx$ is given by:

$$F = H \cdot \frac{dH}{dx} \cdot V(K_o - K_s) \quad (1)$$

where $K_s$ is the net volume magnetic susceptibility of the gas surrounding the element. It will be appreciated that a variation in the partial pressure of a paramagnetic gas in the gas surrounding the element will cause $K_s$ to vary. It therefore follows that the force F on the element given by equation (1) will vary according to the partial pressure of the paramagnetic gas surrounding the element.

If the element is caused to oscillate in the magnetic field, the parameters of the oscillation, such as the damping or the frequency of oscillation are affected by the force F given by equation (1) which in turn is affected by the partial pressure of paramagnetic gas surrounding the element. This is the basis of the present invention.

BRIEF DESCRIPTION OF THE DRAWINGS

In order that the present invention be more fully understood preferred embodiments will be described by way of example with reference to the accompanying drawings, in which.

DESCRIPTION OF THE PREFERRED EMBODIMENT

Suppose an element is suspended within a magnetic field by an elastic member such that there is only one main mode of oscillation and that is in a direction perpendicular to the magnetic field. If the elastic constant of the mounting member is S, then the equation of motion of the oscillation of the element in the absence of external damping is:

$$M\ddot{X} + SX = 0 \quad (2)$$

where M is the mass of the element and X is the displacement. As is well known, the natural frequency, $w_o$, of such a system is given by:

$$w_o = \sqrt{S/M} \quad (3)$$

From equation (3) it can be seen than any factor equivalent to a variation in S or M would alter the natural frequency of the oscillating system.

Figure 1:
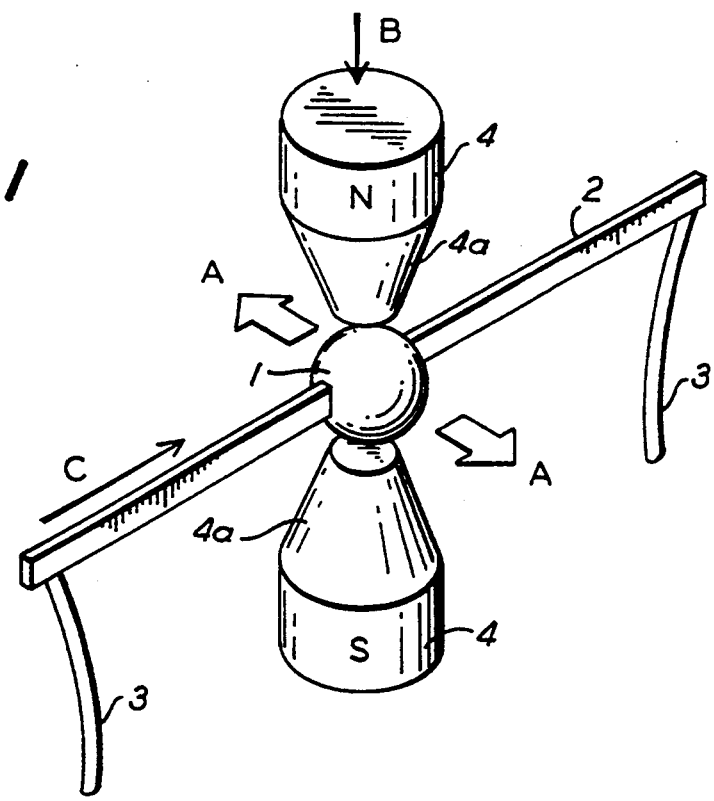
FIG. 1 illustrates basic apparatus operating according to the present invention.

FIG. 1 illustrates an apparatus embodying the features outlined above. The apparatus comprises an element 1, preferably a spherical element, resiliently mounted by way of a metallic strip 2 and springs 3. This arrangement is designed to allow oscillation of the element 1 only in the direction shown by arrows A. The apparatus also comprises permanent magnets 4 having pole pieces 4a which provide a magnetic field in the region of element 1 and strip 2 in the direction of arrow B.

When the gas surrounding element 1 is of low magnetic susceptibility (diamagnetic) such as nitrogen and element 1 is caused to oscillate, there is a low viscous damping force due to the surrounding gas and a low constant damping force F given by equation (1). When the gas surrounding element 1 is of high magnetic susceptibility (paramagnetic) such as oxygen, there is a low viscous damping force virtually identical to that in the presence of the diamagnetic gas. (Oxygen and nitrogen have similar densities). However the constant damping force F given by equation (1) is much greater due to the increase in magnetic susceptibility. This force may be expressed as related to the magnetic force on the oxygen molecules attempting to get into the strong region of the magnetic field and finding the element 1 in the way.

If the suffix '1' designates the situation in the presence of nitrogen and the suffix '2' the situation in the presence of oxygen, then from equation (1):

$$F_1 = H \cdot \frac{dH}{dx} \cdot V(K_o - K_{s1}) \quad (1)$$

$$F_2 = H \cdot \frac{dH}{dx} \cdot V(K_o - K_{s2})$$

and the increase in the force F when oxygen replaces nitrogen is given by:

$$F = F_2 - F_1 \quad (4)$$
$$= H \cdot \frac{dH}{dx} \cdot V(K_{s1} - K_{s2})$$

Typically, the oscillating element 1 has a volume of $4.10 \times 10^{-9}$m (a sphere of $10^{-3}$m radius) and may be made of an essentially non-magnetic material such as perspex ($K_o = -0.3 \times 10^{-11}$). A spherical element is not essential; a flat, rectangular or other geometrical shape element may be used. The field produced by magnets 4 may have a strength H of $0.5 \times 10^6$ Am$^{-1}$ and a gradient of $80 \times 10^6$ Am$^{-2}$ in the region of the element. In the notation above, $K_{s1} = -0.7 \times 10^{-11}$ and $K_{s2} = 191 \times 10^{-11}$ and therefore the magnitude of $K_{s1} - K_{s2}$ is approximately $192 \times 10^{-11}$. This gives the change in force on the element as:

$$F = 0.5 \times 10^6 \times 80 \times 10^6 \times 4.1 \times 10^{-9} \times 192 \times 10^{-11}$$
$$= 300 \ \mu N \text{ (approximately)}$$

The effect of this increase in the constant force acting on the oscillating element may be considered as an added inertia, and hence an effective increase in M in equation (3), or as an enhancement of the damping effect, and will be to affect the frequency of oscillation of the element. The force is directly related to the volume of paramagnetic gas present in the vicinity of the element, and hence is related to the partial pressure of that gas.

The use of an electrically conducting strip 2 for mounting the element 1 allows the passage of electric current along the strip 2 and through element 1. This may be used in two ways during operation of the apparatus.

If an electrical pulse is applied across the ends of strip 2 a transient current flows as indicated by arrow C. This interacts with the magnetic field to cause motion of the strip 2 and element 1 in direction A, and hence starts the element 1 oscillating. Once oscillation of element 1 is in progress, the movement of conductor 2 in the magnetic field induces current in the conductor in direction C. This may be monitored as a varying e.m.f. which gives a direct indication of the frequency and amplitude of the oscillation.

Thus the use of electrically conducting strip 2 provides means both to stimulate the element into oscillation and to observe the amplitude and frequency of this vibration.

The variation in the oscillation of the element may be used in a number of ways to determine the amount of paramagnetic gas present.

a) The increase in force F may be considered as an effective increase in the mass of the oscillating member which results in a change in the natural frequency of the system. Therefore if the oscillating member is coupled to an electronic system and set out to maintain an oscillation in the presence of a non-magnetic gas such as nitrogen, when a paramagnetic gas such as oxygen is introduced in the vicinity of the oscillating member the frequency of the oscillation will be lowered in relation to the concentration of the paramagnetic gas.

The change in frequency could be very small and the use of a very stable reference oscillator or or second vibrating element oscillating in a non-magnetic gas such as nitrogen may be necessary. The beat frequency could then be related to the change in the paramagnetic gas concentration.

b) Alternatively the Q factor of the oscillator system can be measured electronically when an non-paramagnetic gas such as nitrogen is in the vicinity and then when a paramagnetic gas such as oxygen is substituted. The change in the Q value will be related to the concentration of the paramagnetic gas.

Figure 2:
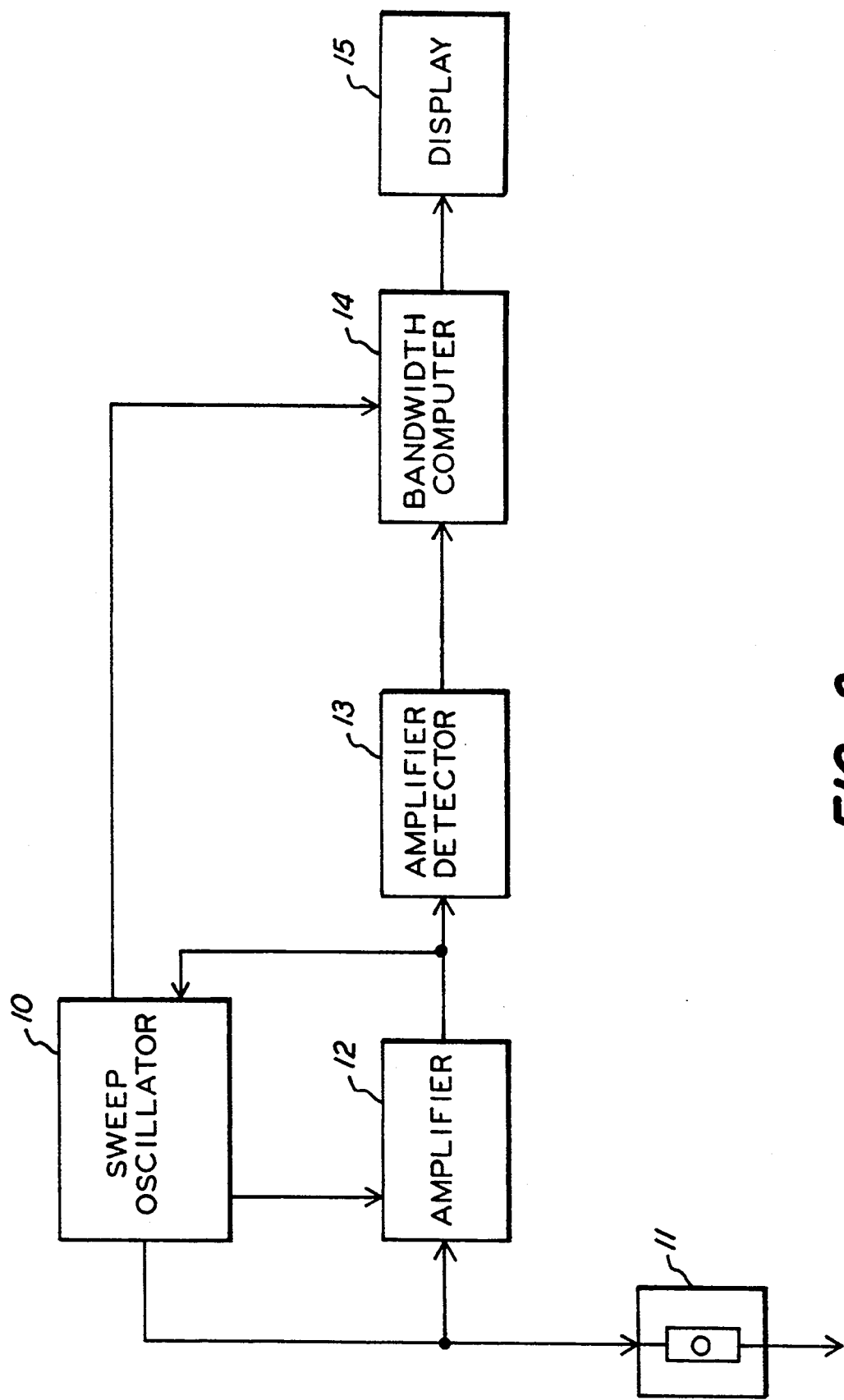
FIG. 2 illustrates a block diagram of one preferred form of control circuitry for use with the apparatus of FIG. 1.

An example of such a system is shown in FIG. 2. Vibrating sensor 11 (the system of FIG. 1) is driven by sweep oscillator (wobulator) 10. An amplifier 12 subtracts an output from the vibrating sensor and an output from sweep oscillator 10. Sweep oscillator 10 frequency locked onto an output from amplifier 12 which is also supplied to amplitude detector 13. Amplitude detector 13 supplies amplitude information to bandwidth computer 14 which also receives frequency information from sweep oscillator 10. The output from bandwidth computer 14 is displayed on display 15.

In this system a sweep oscillator periodically takes the vibrating element through its resonance point and compares the bandwidth at a given amplitude between the nitrogen state and the oxygen state.

c) Yet another alternative would be to start the system oscillating and not maintain the oscillation and observe the decay of the oscillation in the oscillating element. Again this will be related to the concentration of the paramagnetic gas.

The envelope of the decaying oscillation in the presence of oxygen can be compared electronically with that of one in the presence of nitrogen. Alternatively the time taken to reach half of the original amplitude can be compared in the presence of the two gases.

d) Yet another alternative would be to start the system oscillating and maintain the oscillation at a given amplitude under a reference gas (e.g. nitrogen) and set up the electronic system such that when the damping effect of the paramagnetic gas (e.g. oxygen) reduces the amplitude, the system increases its energy input to element so as to keep the monitored amplitude at the same level, the extra amount of energy required to do that being related to the amount of oxygen in the sample gas.

Figure 3:
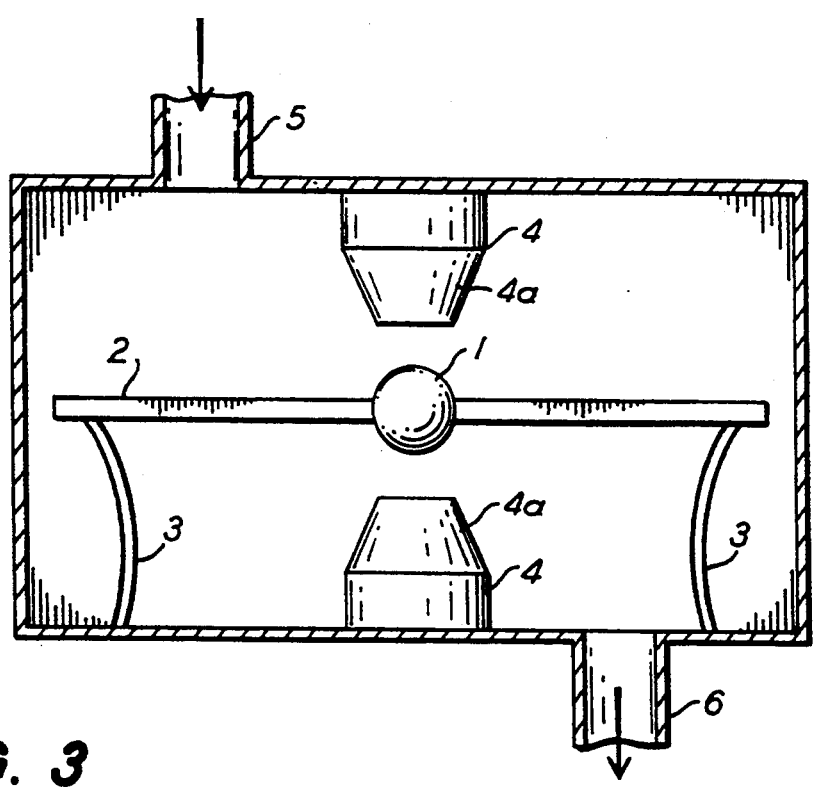
FIG. 3 is a schematic diagram of a flow cell incorporating the apparatus of FIG. 1.

FIG. 3 is a schematic diagram illustrating the use of the apparatus of FIG. 1 in a flow cell. The same numerals designate corresponding parts, and the cell is provided with a gas inlet 5 and a gas outlet 6. Such a cell may be installed in any gas line to monitor the gas flowing through the line. The proportion of paramagnetic gas surrounding element 1 may be determined as discussed above at time intervals or continuously whereby to monitor the amount of paramagnetic gas flowing in the line. The inlet and/or outlet configuration may be specifically designed to prevent the physical flow of gas affecting the oscillation of the element.

Apparatus according to this invention may be used to test a variety of samples, e.g. solvents, corrosive gases or inert gases. The oscillating element may be made of any suitable material, e.g. plastic or glass, depending on the nature of the sample to be tested.

I claim:

1. A method of determining the proportion of a paramagnetic gas in a mixture of gases comprising:
    providing a magnetic field and a resiliently mounted member in said magnetic field;
    causing said resiliently mounted member to oscillate;
    determining a value of at least one specified parameter of the oscillation whereby to determine the proportion of a paramagnetic gas in the mixture of gases surrounding said resiliently mounted member.

2. The method of claim 1 wherein one of the said at least one specified parameters is the damping of the oscillation.

3. The method of claim 2 wherein the resiliently mounted member is mounted by means of a strip having its longitudinal axis substantially perpendicular to the magnetic field.

4. The method of claim 3 wherein the strip is electrically conductive and oscillation of the resiliently mounted member may be caused by passing electric current along said strip.

5. The method of claim 1 wherein one of the said at least one specified parameters is the frequency of the oscillation.

6. The method of claim 5 wherein the resiliently mounted member is mounted by means of a strip having its longitudinal axis substantially perpendicular to the magnetic field.

7. The method of claim 6 wherein the strip is electrically conductive and oscillation of the resiliently mounted member may be caused by passing electric current along said strip.

8. The method of claim 1 wherein one of the said at least one specified parameters is the Q factor of the oscillation.

9. The method of claim 8 wherein the resiliently mounted member is mounted by means of a strip having its longitudinal axis substantially perpendicular to the magnetic field.

10. The method of claim 9 wherein the strip is electrically conductive and oscillation of the resiliently mounted member may be caused by passing electric current along said strip.

11. The method of claim 1 wherein one of the said at least one specified parameters is the energy required to be supplied to the oscillating system to maintain the oscillation.

12. The method of claim 11 wherein the resiliently mounted member is mounted by means of a strip having its longitudinal axis substantially perpendicular to the magnetic field.

13. The method of claim 12 wherein the strip is electrically conductive and oscillation of the resiliently mounted member may be caused by passing electric current along said strip.

14. The method of claim 1 wherein the resiliently mounted member is mounted by means of a strip having its longitudinal axis substantially perpendicular to the magnetic field.

15. The method of claim 14 wherein the strip is electrically conductive and oscillation of the resiliently mounted member may be caused by passing electric current along said strip.

16. Apparatus for determining the proportion of a paramagnetic gas in a gas flow comprising:
    means defining a chamber having an inlet and an outlet for said gas flow;
    means providing a magnetic field within said chamber;
    a testing element;
    means resiliently mounting said testing element in said magnetic filed and within said chamber;
    means for causing said testing element to oscillate; and
    means for determining a value of at least one specified parameter of the oscillation whereby to determine the proportion of a paramagnetic gas in the gas mixture in the chamber and surrounding the testing element.

17. Apparatus as defined in claim 16 in which the testing element is spherical.

18. Apparatus as defined in claim 17 in which the testing element comprises a plastic material.

19. Apparatus as defined in claim 18 in which the testing element is mounted by way of a strip having its longitudinal axis substantially perpendicular to the magnetic field.

20. Apparatus as defined in claim 17 in which the testing element comprises glass.

21. Apparatus as defined in claim 20 in which the testing element is mounted by way of a strip having its longitudinal axis substantially perpendicular to the magnetic field.

22. Apparatus as defined in claim 17 in which the testing element is mounted by way of a strip having its longitudinal axis substantially perpendicular to the magnetic field.

23. Apparatus as defined in claim 22 in which the strip is electrically conductive and the means for causing the testing element to oscillate comprises means for passing an electric current along said strip.

24. Apparatus as defined in claim 8 in which the testing element comprises a plastic material.

25. Apparatus as defined in claim 24 in which the testing element is mounted by way of a strip having its longitudinal axis substantially perpendicular to the magnetic field.

26. Apparatus as defined in claim 8 in which the testing element comprises glass.

27. Apparatus as defined in claim 26 in which the testing element is mounted by way of a strip having its longitudinal axis substantially perpendicular to the magnetic field.

28. Apparatus as defined in claim 16 in which the testing element is mounted by way of a strip having its longitudinal axis substantially perpendicular to the magnetic field.

29. Apparatus as defined in claim 28 in which the strip is electrically conductive and the means for causing the testing element to oscillate comprises means for passing an electric current along said strip.

* * * * *